United States Patent [19]
De Boer et al.

[11] Patent Number: 5,886,107
[45] Date of Patent: Mar. 23, 1999

[54] PROCESS FOR HYDROGENATION OF CONJUGATED DIENE POLYMERS AND CATALYST COMPOSITIONS SUITABLE FOR USE THEREIN

[75] Inventors: Eric Johannes Maria De Boer; Bart Hessen; Adriaan Albert Van Der Huizen; Wouter De Jong; Adrianus Johannes Van Der Linden; Bart Johan Ruisch; Lodewijk Schoon; Heleen Johanna Augusta De Smet; Frederik Hendrik Van Der Steen; Hubertus Cornelis Thomas Lucianes Van Strien; Alan Villena; Judith Johanna Berendina Walhof, all of Amsterdam, Netherlands

[73] Assignee: Shell Oil Company, Houston, Tex.

[21] Appl. No.: 864,602

[22] Filed: May 28, 1997

[30] Foreign Application Priority Data

May 29, 1996 [EP] European Pat. Off. ............. 96303815

[51] Int. Cl.$^6$ .......................................... C08F 8/04
[52] U.S. Cl. ....................... 525/338; 502/103; 525/332.8; 525/332.4; 525/333.1; 525/333.2; 525/334
[58] Field of Search ................................... 525/338, 334; 502/103

[56] References Cited

U.S. PATENT DOCUMENTS

| | | | |
|---|---|---|---|
| 3,663,635 | 5/1972 | Lassau et al. | 260/666 P |
| 4,501,857 | 2/1985 | Kishimoto et al. | 525/338 |
| 5,039,755 | 8/1991 | Chamberlain et al. | 525/338 |
| 5,242,986 | 9/1993 | Gibler et al. | |
| 5,434,116 | 7/1995 | Sone et al. | |
| 5,541,272 | 7/1996 | Schmid et al. | 526/160 |

FOREIGN PATENT DOCUMENTS

| | | |
|---|---|---|
| 1007262 | 5/1995 | Belgium . |
| 0434469A2 | 12/1990 | European Pat. Off. . |
| 0532099A | 9/1992 | European Pat. Off. . |
| 0544304A | 11/1992 | European Pat. Off. . |
| 0545844A1 | 12/1992 | European Pat. Off. . |
| 0549063A | 12/1992 | European Pat. Off. . |
| 0601953A1 | 11/1993 | European Pat. Off. . |
| 638593 | 2/1995 | European Pat. Off. . |
| 2159819A | 4/1984 | United Kingdom . |
| 95/25136 | 3/1994 | WIPO . |

OTHER PUBLICATIONS

"Preparation and X–ray Structure of a Novel Chiral Methylene Bridged Titanocene Complex", by Christopher A. Willoughby, William M. Davis, Stephen L. Buchwald, *Journal of Organometallic Chemistry 497*, (1995) pp. 11–15.

G.S. Sodic et al.: "Halide and complex halogero anions..." Journal of Organometallic Chemistry., vol. 238, No. 2, 1982, Lausanne CH, pp. 117–183, XP002040972.

"Mechanism of Acetylene Polymerization of the $NiCl_2–NaBH_4$ System in Alcohols", by N. S. Gorkova, F. S. Diachkovski an P. E. Matkovski, *Vysokomol, Soedin, Ser.* B, vol. 20, No. 10, 1978, pp. 774–777.

*Primary Examiner*—Bernard Lipman

[57] ABSTRACT

The invention provides a catalyst composition suitable for hydrogenation of polymers containing ethylenical unsaturation which comprises at least:

(a) a titanium compound of the formula

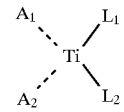

wherein $A_1$ represents an optionally substituted heterocyclic five membered ring comprising a phosphorous or nitrogen heteroatom, and $A_2$ has the same meaning as $A_1$ or alternatively represents an optionally substituted cyclopentadienyl group or indenyl group, and wherein $L_1$ and $L_2$ may be the same or different and each may be selected from hydrogen, halogen, lower alkyl, phenyl, aralkyl, having from 7 to 10 carbons, lower alkoxy group, phenyloxy, phenylalkoxy group having from 7 to 10 carbon atoms, carboxyl, carbonyl, a ~$CH_2P(Phenyl)_2$, —$CH_2 Si(lower alkyl)_3$ or ~$P(phenyl)_2$ group; and (b) an alkalimetal hydride, added as such or prepared in situ in the polymer solution from the alkalimetal terminated living polymer and/or from additionally added alkalimetal alkyl. The invention further provides a process for hydrogenation of polymers containing ethylenical unsaturation.

15 Claims, No Drawings

PROCESS FOR HYDROGENATION OF CONJUGATED DIENE POLYMERS AND CATALYST COMPOSITIONS SUITABLE FOR USE THEREIN

FIELD OF THE INVENTION

The present invention relates to a process for the hydrogenation of conjugated diene polymers and catalyst compositions suitable for use therein, more particularly to a process for the hydrogenation of polymers and copolymers of conjugated diene polymers, using a hydrogenation catalyst composition comprising at least a titanium compound and a alkali metal compound.

SUMMARY OF THE INVENTION

Numerous catalyst are known for the hydrogenation of compounds containing unsaturated double bonds, catalysts which may be classified into two groups:

(1) Heterogeneous catalysts, generally consisting of a metal such as Ni, Pd, Pt, Ru, etc. optionally deposited on a support such as carbon, silica, alumina, calcium carbonate, etc.; and (2) homogeneous catalysts such as (a) Ziegler catalysts consisting of a combination of an organic salt of Ni, Co, Fe, Cr, etc. and a reducing agent such as for instance organoaluminium compounds, and (b) single component organometallic compounds of Ru, Rh, Ti, La, etc.

Heterogeneous catalysts are widely used in industry, but compared with the homogeneous catalyst they are less active and hence, in order to carry out the desired hydrogenation with these heterogeneous catalysts, large quantities of catalyst are needed and the reaction must be carried out at relatively high pressures and temperatures. The homogeneous catalysts are generally more active; a small amount of catalyst is sufficient, and the hydrogenation reaction can be carried out under milder pressure and temperature conditions.

Polymers of conjugated dienes such as 1,3-butadiene and isoprene and the copolymers of these dienes with vinylaromatic monomers, e.g. with styrene, are widely used in industry as elastomers. These polymers contain double bonds in their chain, which permit their vulcanization, but whose presence causes a low resistance to ageing and oxidation. Some block copolymers of conjugated dienes and vinylaromatic hydrocarbons are used without vulcanization as thermoplastic elastomers, as transparent impact-resistant resins, or as modifiers or compatibilisers of polystyrene and polyolefin resins. However, these copolymers have a low resistance to ageing and oxidation by atmospheric oxygen and by ozone, due to the presence of double bonds in their chain. Hence, the use of these copolymers in applications requiring exposure to the external environment is limited. The resistance to oxidation by oxygen and ozone, and, in general, the resistance to ageing, may be considerably improved by hydrogenating these polymers to obtain total or partial saturation of the double bonds. Numerous processes have been proposed for the hydrogenation of polymers which contain olefinic double bonds. Two types of processes are generally involved: those which use the aforementioned supported heterogeneous catalysts, and those using homogeneous catalysts of the Ziegler type or organometallic compounds of rhodium and titanium.

In the processes using supported heterogeneous catalysts, the polymer to be hydrogenated is first dissolved in a suitable solvent and then contacted with hydrogen in the presence of the heterogeneous catalyst. The contact of the reactants with the catalyst is difficult due to the relatively high viscosity of the polymer solution, to steric hindrances of the polymer chain, and to the high adsorption of the polymer which, once hydrogenated, tends to remain on the surface of the catalyst, interfering with the access to the active centres of the nonhydrogenated polymer. Hence, to achieve complete hydrogenation of the double bonds, large quantities of catalyst and severe reaction conditions are required. Usually this causes decomposition and gelification of the polymer. Furthermore, in the hydrogenation of copolymers of conjugated dienes with vinylaromatic hydrocarbons the aromatic nuclei are also hydrogenated, and it is difficult to effect a selective hydrogenation of the double bonds of the polydiene units. Likewise, the physical separation of the catalyst from the solution of hydrogenated polymer is extremely difficult, and in some cases a complete elimination is impossible due to the strong adsorption of the polymer on the heterogeneous catalyst.

In processes using Ziegler-type catalytic systems (as mentioned hereinbefore), the reaction takes place substantially in a homogeneous medium, and hence the hydrogenation of copolymers may be carried out under mild pressure and temperature conditions. Moreover, by adequately selecting the conditions of hydrogenation it is possible to selectively hydrogenate the double bonds of the poly(conjugated diene) blocks and without hydrogenating the aromatic rings of the poly(vinylaromatic hydrocarbon) blocks.

Nevertheless the elimination of the catalyst residues from the reaction product—which is absolutely necessary because these residues have an unfavourable effect on the stability of the hydrogenated polymers—is a complicated and costly step.

Other processes using other homogeneous catalysts, e.g. the rhodium compounds described in U.S. Pat. No. 3,898,208 and in the Japanese patent JP 01,289,805 have the disadvantage of the high cost of the rhodium catalysts.

It is known that hydrogenation catalysts in which one of the components is a derivative of cyclopenta-dienyltitanium (U.S. Pat. No. 4,501,857) are used—necessarily in the presence of organolithium compounds—for the hydrogenation of the olefinic double bonds of the polymers of conjugated dienes.

European Patent application 0460725 describes the use of a similar catalyst system for the hydrogenation of polymers that had been synthesised by means of an organolithium compound and which have been terminated by the addition of hydrogen, the presence of the lithium hydride formed in the final reaction being necessary in this case to generate an active catalyst. The examples of both publications use the compound bis(cyclopentadienyl) titanium dichloride ($Cp_2TiCl_2$).

In the European patent application nos. 0549063 A and 0532099 A further improvements of this conception were described, using an alkali metal hydride to titanium molar ratio in the terminated polymer solution of at least 6:1 and using an alkyl benzoate as additional promoter during the hydrogenation.

The examples of these beforementioned publications actually used the compound $Cp_2TiCl_2$ only, which appeared to be very sparingly soluble in industrially applied solvents.

In British Patent Application No. 2,159,819 A it is indicated that species of the $Cp_2TiR_2$ type (R=alkylaryl groups) are catalysts capable of selectively hydrogenating the double bonds of polymers and co-polymers of conjugated dienes, without requiring the presence of an organolithium compound.

European Patent Application No. 0434469 A2 describes the use of an extraordinarily complex catalytic system, comprising a bis-cyclopentadienyl-titanium compound in combination with an organometallic compound of aluminium or magnesium and alkaline metals in the presence of alkoxides of alkaline metals and polar compounds of the ether, ketone, sulfoxide, etc. type. Said catalytic system is capable of hydrogenating the double bonds of polymers and copolymers of conjugated dienes.

An alleged further improvement of the latter conception has been described in European Patent application no. 0544304 A, using a catalyst composition comprising:

(a) a bis(cyclopentadienyl) transition metal compound and in particular bis(cyclopentadienyl) titanium dichloride or bis(cyclopentadienyl) titanium dibenzyl;

(b) at least one polar compound selected from the group consisting of carbonyl group-containing compounds and epoxy group containing compounds, and in particular esters of a monobasic acid or dibasic acid, lactone compounds, lactam compounds and epoxy compounds such as glycidyl methyl ether, glycidyl n-butyl ethers, glycidyl allyl ether, glycidyl methacrylate, glycidyl acrylate; 1,2-butylene oxide, cyclohexene oxide; and (c) an organic lithium compound and in particular n-butyllithium, sec-butyllithium, t-butyllithium, phenyllithium, n-hexyllithium, p-tolyllithium, xylyllithium, 1,4-dilithiobutane, alkylenedilithium and living polymers having lithium at their terminals; and preferably in addition (d) a reducing organometal compound selected from the group consisting of aluminium compounds, zinc compounds and magnesium compounds, such as triethyl aluminium, tri-i-butylaluminium, diethyl aluminium chloride, ethyl aluminium, diethyl aluminium chloride, ethyl aluminium dichloride, aluminium, tri-i-propoxide and aluminium tri-t-butoxide. The molar ratio between the components (a) and (b) has been indicated to be smaller than 1/0.5 and more preferably in the range of from 1/2 to 1/30; the molar ratio between the components (a) and (c) has been indicated to be in the range of from 1/1 to 1/40 and most preferably in the range of from 1/3 to 1/30.

Further alleged improvements, emanating from this conception of the use of titanium compounds as hydrogenation catalyst ingredients, have been described in the European Patent Applications nos. 0545844 A and 0601953 A, wherein the cyclopentadienyl ligands have been fully methylated or have been linked together by a dimethylsilylene group and wherein the other ligands R represent an alkoxide group, containing from 1 to 20 carbon atoms, or a halogen atom or $CH_2PPh_2$, $PPh_2$ or $CH_2SiMe_3$ or PhOR ligands.

However, said processes did not provide any significant advantage over the earlier discussed prior art.

To obtain more economical hydrogenation processes, present-day industry feels the need of having homogeneous catalysts available which are more effective that those currently known, which are stable, and active in concentrations that are sufficiently low so as to be able to avoid the costly step of elimination of catalyst residues from the hydrogenated polymer.

SUMMARY OF THE INVENTION

One object of the present invention is formed by an improved hydrogenation process.

Another object of the present invention is formed by a catalyst composition to be used for said process.

The present invention relates to a catalyst composition for hydrogenation of polymers containing ethylenical unsaturation, which comprises at least:

(a) a titanium compound of the formula

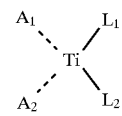

wherein $A_1$ represents an optionally substituted heterocyclic five membered ring comprising a phosphorous or nitrogen heteroatom, and $A_2$ has the same meaning as $A_1$ or alternatively represents an optionally substituted cyclopentadienyl group or indenyl group, and wherein $L_1$ and $L_2$ may be the same or different and each may be selected from hydrogen, halogen and preferred chlorine, lower alkyl, phenyl, aralkyl, having from 7 to 10 carbons, lower alkoxy group, phenyloxy, phenylalkoxy group having from 7 to 10 carbon atoms, carboxyl, carbonyl, a $\sim CH_2P(Phenyl)_2$, $-CH_2Si(\text{lower alkyl})_3$ or $\sim P(phenyl)_2$ group; and (b) an alkali metal hydride, added as such or prepared in situ in the polymer solution from the alkali metal terminated living polymer and/or from additionally added alkali metal alkyl.

DETAILED DESCRIPTION OF THE PRESENT INVENTION

The molar ratio of the alkali metal:titanium in the catalyst composition of the present invention is preferably at least 2:1.

As alkali metal hydride is preferably used lithium hydride. The polymerisation initiator to be used for the starting living polymer of at least one conjugated diene and the optional additional amounts of alkali metal compound to form additional alkali metal hydride are preferably organolithium compounds. They are preferably selected from methyllithium, ethyllithium, n-propyl lithium, n-butyllithium, sec-butyl lithium, tert butyl lithium, n-hexyllithium, phenyl lithium, p-tolyl lithium, xyllithium, 1,4-dilithiobutane, alkylene dilithium or a reaction product of butyl lithium and divinyl benzene.

Particularly preferred are n-butyl lithium, sec butyl lithium, tert-butyl lithium and phenyllithium. Most preferred are tert butyllithium, sec-butyllithium or n-butyllithium. The molar ratio of lithium hydride to titanium in the catalyst composition is more preferably at least 6 and most preferably in the range of from 6 to 25.

The titanium compound (a) is normally used in amounts of from 5 to 100 mg per kg of conjugated diene polymer to be hydrogenated, and preferably in amounts from 20 to 60 mg/kg of conjugated diene polymer to be hydrogenated.

Preferred ligands $L_1$ and $L_2$ in component (a) are selected from chlorine, bromine, carbonyl, methyl, ethyl, n-propyl, isopropyl, n-butyl, tert-butyl, sec-butyl, trimethylsilyloxy, benzyl, phenyl, hexyl, methoxy, ethoxy, n-propoxy, isopropoxy, butoxy, tert butoxy, sec butoxy, pentoxy, neopentoxy, phenoxy, phenylmethoxy, phenylethoxy and a $CH_2P(phenyl)_2$ group.

More preferably $L_1$ and $L_2$ in the titanium catalyst component are both chlorine, benzyl, phenyl, methoxy, ethoxy, isopropoxy, tert-butoxy, n-butoxy, phenoxy or $CH_2P(phenyl)_2$ group, and most preferably both are chlorine.

The heterocyclic five membered ring, the cyclopentadienyl or the indenyl ring may optionally be substituted by one or more of the same or different groups, which may be selected from halogen or phenyl which optionally may bear one or more the same or different substituents, lower alkyl, alkoxy, phenoxy, phenylalkoxy, benzyl and a bulky substituent containing one or more hetero atoms such as tri(loweralkyl)silyl, ~NPh$_2$, ~NHPh, ~BPh$_2$ and ~B(OPh)$_2$.

When one or more, and preferably one or two, of the symbols R represent phenyl, this may optionally be substituted by one or more substituents selected from lower alkyl, halogen, preferably fluoro or chloro, and lower alkoxy.

Examples thereof are para-tert butylphenyl, pentafluorophenyl, dichlorophenyl, 3,5 di(t-butyl)-4-methoxy phenyl, trifluorophenyl.

With the terms "lower alkyl" and "lower alkoxy" as used throughout this specification, is meant that these groups contain from 1 to 4 carbon atoms.

The most preferred titanium compounds are (1-indenyl) (2,4-dimethylphospholyl) titanium dichloride, (1-indenyl) (2,4-dimethylphospholyl) titanium diphenoxide, (indenyl) (2,4-dimethylphospholyl) titanium dimethoxide, (cyclopentadienyl)(2,4-dimethylphospholyl) titanium dichoride (cyclopentadienyl)(2,4-phenyl phospholyl) titanium dichloride, (cyclopentadienyl)(2,4-dimethylphospholyl) titanium dimethoxide, (cyclopentadienyl)(2,4phenyl-phospholyl)titanium dimethoxide, (2-methyl-cyclopentadienyl)(2,4-dimethylphospholyl) titanium dichloride, (dimethoxycyclopentadienyl)(2,4-dimethylphospholyl) titanium dimethoxide, (2,4-dimethylcyclopentadienyl)(2,4-dimethylphospholyl) titanium dichloride, (1-methylindenyl) (2,4-dimethyl phospholyl) titanium dichloride, (5,6-dimethoxyindenyl) (2,4dimethyl phospholyl)titanium dimethoxide, 1(methylindenyl)(2,4-dimethyl phospholyl) titanium dichloride, (5,6-dimethoxyindenyl)(2,4-diphenyl phospholyl) titanium dimethoxide, (1-methylindenyl) (phospholyl) titanium dimethoxide, and (1-methylindenyl) (phospholyl) titanium dichloride.

It will be appreciated that another aspect of the present invention is formed by a process for the hydrogenation of polymers containing ethylenical unsaturation (double C—C bonds) by bringing a polymer solution in intensive contact with hydrogen in the presence of at least the catalyst components (a) and (b).

According to a more preferred embodiment of the hydrogenation process of the present invention one or more promoters (c) may be present in addition to the beforementioned catalyst components (a) and (b).

Said promoters (c) can be selected from polar ketone compounds, hydroxy group containing ketone compounds, aldehyde compounds, ester compounds, lactone compounds, lactam compounds and epoxy compounds, or from a reducing organometal compound selected from the group consisting of aluminium compounds, zinc compounds and magnesium compounds.

Of the beforementioned promoters especially preferred are ketone compounds, hydroxy group-containing ketone compounds, aldehyde compounds, ester compounds and epoxy compounds.

Specific examples of preferred ketone compounds include acetone, diethyl ketone, di-n-propyl ketone, di-i-propyl ketone, di-sec-butyl ketone, di-t-butyl ketone, methyl ethyl ketone, i-propyl methyl ketone, i-butyl methyl ketone, 2-pentanone, 3-hexanone, 3-decanone, diacetyl, acetophenone, 4'-methoxy acetophenone, 4'-methyl acetophenone, propiophenone, benzophenone, 4-methoxy benzophenone, 4,4'-dimethoxy benzophenone, benzyl phenyl ketone, benzil acetone, benzoyl acetone, cyclopentanone, cyclohexanone, 4-methyl cyclohexanone, 1,2-cyclohexane dione, cycloheptanone, and acetyl acetone.

Hydroxy group-containing ketone compounds are defined as compounds having both a hydroxy group and a ketone carbonyl group in the molecule. Specific examples of preferred compounds are hydroxyacetone, acetoin, 4-hydroxy-2-butanone, 3-hydroxy-3-methyl-2butanone, 5-hydroxy-2-butanone, diacetone alcohol, 4-(p-hydroxyphenyl)-2-butanone, 2-hydroxyacetophenone, 2'-hydroxyacetophenone, 3'-hydroxyacetophenone, 4'-hydroxyacetophenone, 4'-hydroxy-3'-methoxyaceto-phenone, 2-hydroxyphenyl ethyl ketone, 4'-hydroxy-propiophenone, 2',4'-dihydroxyacetophenone, 2,',5'-dihydroxy-acetophenone, 2',6'-dihydroxyaceto-phenone, 3',5'-dihydroxyacetophenone, 2',3',4'-trihydroxy-acetophenone, 2-hydroxybenzophenone, 4-hydroxybenzo-phenone, 2-hydroxy-4-methoxybenzophenone, 2-hydroxy-4-n-octyloxybenzophenone, 2,2'-dihydroxybenzophenone, 2,4-dihydroxybenzophenone, 4,4'-dihydroxybenzophenone, 2,2'dihydroxy-4-methoxybenzo-phenone, 2,,4'-trihydroxybenzophenone, and benzoin.

As aldehyde compounds, either aliphatic or aromatic aldehyde compounds can be used. The aliphatic group in aliphatic aldehyde compounds may be either saturated or unsaturated and either linear or branched. Given as examples of preferable aldehyde compounds are formaldehyde, acetaldehyde, propionaldehyde, n-butylaldehyde, i-butylaldehyde, n-valeraldehyde, i-valeraldehyde, pivalaldehyde, n-capronaldehyde, 2-ethylhexyladehyde, n-heptaldehyde, n-caprylaldehyde, pelargonaldehyde, n-caprinaldehyde, n-undecylaldehyde, laurylaldehyde, tridecylaldehyde, myristylaldehyde, pentadecylaldehyde, palmitylaldehyde, margarylaldehyde, stearylaldehyde, glyoxal, succinaldehyde, benzaldehyde, o-tolualdehyde, m-tolualdehyde, p-tolualdehyde, α-naphthaldehyde, β-naphthaldehyde, and phenylacetnaphthaldehtde.

Examples of ester compounds are esters formed by a monobasic acid, e.g. formic acid, acetic acid, propionic acid, butyric acid, capronic acid, pelargonic acid, lauric acid, palmitic acid, stearic acid, isostearic acid, cyclohexylpropionic acid, cyclohexyl-capronic acid, benzoic acid, phenylbutyric acid, etc., a dibasic acid, e.g., oxalic acid, maleic acid, malonic acid, fumaric acid, succinic acid, glutaric acid, adipic acid, pimelic acid, suberic acid, sebacic acid, itaconic acid, phthalic acid, isophthalic acid, terephthalic acid, azelaic acid, etc., or apolybasic acid, e.g., 1,2,3-propanetricarboxylic acid, 1,3,5-n-pentanetricarboxylic acid, etc., 1,3,5-n-pentanetricarboxylic acid, etc., and an alcohol, ee.g., methyl alcohol, ethyl alcohol, isopropyl alcohol, n-butyl alcohol, sec-butyl alcohol, tert-butyl alcohol, amyl alcohol, hexyl alcohol, octyl alcohol, phenol, cresol, 1,3-butanediol, 1,4-butanediol, piniacol, pentaerythritol, etc.

Specific examples of lactone compounds are β-propiolactone, γ-butyrolactone, ε-caprolactone. Δα, β-crotonlactone, Δβ,γ-crotonlactone, coumarin, phthalide, α-pyrone, sydonone, and fluoran.

Given as specific examples of lactam compounds are β-propiolactam, 2-pyrrolidone, 2-piperidone, ε-caprolactam, n-heptanelactam, 8-octanelactam, 9-nonanelactam, 10-decanelactam, 2-quinolone, 1-isoquinolone, oxinedole, iso-indigo, isatin, hydantoin, and quinolidinone.

Specific examples of preferably epoxy compounds include 1,3-butadiene monoxide, 1,3-butadiene dioxide, 1,2-butylene oxide, 2,3-butylene oxide, cyclohexene oxide, 1,2-epoxy cyclododecane, 1,2-epoxy decane, 1,2-epoxy eicosane, 1,2-epoxy heptane, 1,2-epoxy hexadecane, 1,2- epoxy octadecane, 1,2-epoxy octane, ethylene glycol diglycidyl ether, 1,2-epoxy heptane, 1,2-epoxy tetradecane, hexamethylene oxide, isobutylene oxide, 1,7-octadiene diepoxide, 2-phenylpropylene oxide, propylene oxide, trans-stilbene oxide, styrene oxide epoxylated 1,2-polybutadiene, epoxylated linseed oil, glycidyl methyl ether, glyciyl n-butyl ether, glycidyl allyl ether, glycidyl methacrylate, and glycidyl acrylate.

A suitable molar ratio of component (a) to component (c) consisting of a polar ketone compound, hydroxy ketone compound, aldehyde compound, ester compound, lactone compound, lactam compound or epoxy compound is in the range of from 10 to 1/2 and more preferably in the range of from 5 to 1 and most preferably in the range of from 2 to 1.

A reducing organic metal compound selected from the group consisting of aluminium compounds, zinc compounds, and magnesium compounds can be used. Given as specific examples are: as aluminium compounds, trimethyl aluminium, triethyl aluminium, tri-i-butyl aluminium, triphenyl aluminium, diethyl aluminium chloride, ethyl aluminium sesquichloride, diethyl aluminium hydride, di-i-butyl aluminium hydride, tri(2-ethylhexyl) aluminium, aluminium tri-i-propoxide, aluminium tri-ti-butoxide, and diethyl aluminium ethoxide; as zinc compounds, diethyl zinc, bis(cyclopentadienyl) zinc, and diphenyl zinc; and as magnesium compounds, dimethyl magnesium, diethyl magnesium, methyl magnesium bromide, methyl magnesium chloride, ethyl magnesium bromide, ethyl magnesium chloride, phenyl magnesium bromide, phenyl magnesium chloride, and t-butyl magnesium chloride.

Beside these compounds, compounds containing two or more reducing metals, such a lithium aluminium hydride, can be used as component (c).

Of the above compounds, triethyl aluminium, tri-i-butyl aluminium, diethyl aluminium chloride, ethyl aluminium dichloride, aluminium tir-i-propoxide, and aluminium tri-t-butoxide are preferred from the aspect of their ready availability and handling easiness. The molar ratio of component (a) and (c) is preferably greater than 1/20, more preferably in the range of from 1/1 to 1/18 and most preferably in the range of from 1/2 to 1/15.

Polymers with a high degree of hydrogenation can be obtained according to the process of the present invention, wherein the catalyst system has been surprisingly found to show a significantly higher activity in combination with a high selectivity, resulting in a higher hydrogenation rate of the starting polymer or enabling the use of a smaller concentration of catalyst per part by weight of polymer, as compared with prior art homogeneous Ti catalyst hydrogenation processes. Moreover this catalyst can be dosed more accurately and shows and excellent reproductivity.

A clear advantage of the process of the present invention is formed by the fact that there seems to be not any distinction during hydrogenation between different types of double C—C bonds, i.e. those in 1,2 vinyl pendant groups, those in the backbone chain without substituted C atoms involved, and those in the backbone chain with substituted C-atoms involved.

As the catalyst system in the present process can be applied in a significantly lower concentration, its concentration in the final hydrogenated product is much lower. The hydrogenation process can be performed at partial hydrogen pressures in the range of from 1 to 50 bar and preferably in the range of from 1 to 35 bar.

Included in the olefinically unsaturated polymers to be hydrogenated by the catalyst composition of the present invention are all polymers containing olefinically carbon-carbon unsaturated double bonds in the polymer main chain or side chains. Typical examples are conjugated diene polymers and random, block, or graft polymers of conjugated diene and olefin.

Included in the above conjugated diene polymers are conjugated diene homopolymers and copolymers produced from conjugated dienes or from at least one conjugated diene and at least one olefin copolymerisable with the conjugated diene.

Given as typical examples of conjugated dienes used for the production of these conjugated diene polymers are conjugated dienes having 4–12 carbon atoms. Specific examples are 1,3-butadiene, isoprene, 2,3-dimethyl-1, 3-butadiene, 1,3-pentadiene, 2-methyl-1, 3-pentadiene, 1,3-pentadiene, 1,3-hexadiene, 4,5-diethyl-1,3-octadiene, 3-butyl-1,3-butyl-1, 3-octadiene, and chloroprene.

From the aspect of manufacturing elastomers having superior characteristics and industrial advantages, 1,3-butadiene and isoprene are particularly preferably. Elastomers, such as polybutadiene, polyisoprene, butadiene/isoprene copolymers are especially preferred polymer materials used in the present invention. There are no specific limitations as to the microstructures of the polymers. All these polymers are suitable materials in the application of the hydrogenation using the catalyst composition of the present invention.

The above-mentioned copolymers produced from at least one conjugated diene and at least one olefin copolymerisable with the conjugated diene are also suitable polymer materials to which the hydrogenation using the catalyst composition of the present invention is applied.

The above-described conjugated diene monomers can be used for the manufacture of this type of copolymers. Any olefins copolymerisable with these conjugated dienes are useable for the manufacture of the copolymer, with vinyl-substituted aromatic hydrocarbons being particular preferred.

Copolymers of the conjugated dienes and vinyl-substituted aromatic hydrocarbons are of particular importance for the production of industrially useful and valuable elastomers or thermoplastic elastomers. Given as specific examples of vinyl-substituted aromatic hydrocarbons used in the manufacture of this type of copolymers are styrene, a-methylstyrene, p-methylstyrene, divinylbenzene, 1,1-diphenylethylene, N,N-dimethyl-p-aminoethylstyrene, N,N-diethyl-p-amionethylstyrene, and vinylpyridine. Of these styrene and α-mehtylstyrene are particular preferred. Specific copolymers providing industrially valuable hydrogenated copolymers are butadiene/styrene copolymer, isoprene/styrene copolymer, and butadiene/α-methylstyrene copolymer.

These copolymers include random copolymers in which monomers are randomly distributed throughout the polymers, progressively reducing block copolymers, complete block copolymers, and graft copolymers and preferably butadiene-styrene block copolymer, isoprene-styrene block copolymers or butadiene/isoprene-styrene block copolymer of linear or radial, muttiarmed shape.

In order to manufacture industrially useful thermoplastic elastomers, a preferable amount of vinyl-substituted aromatic hydrocarbons is in the range of from 15 to 45% by weight.

A content of vinyl bonds in the conjugated diene units of 10% or more of the total conjugated diene units is desirable for obtaining hydrogenated polymers with superior characteristics.

Included also in polymers which can be used in the hydrogenating process using the catalyst composition of the present invention are those of linear type, as well as branched type or radial or star type produced by coupling using a coupling agent.

Also included in the polymers to be hydrogenated according to the present invention are those having terminals modified with polar groups after the living anionic polymerisation or by other means. Hydroxy group, carboxyl group, ester group, isocyanate group, urethane group, amide group, ureas group, and thiourethane group can be used as the polar group.

Beside the above-mentioned polymers, any polymer manufactured by any polymerisation methods, e.g., anion polymerisation, cation polymeristion, co-ordination polymerisation, radical polymerisation, solution polymerisation, or emulsion polymerisation can be used in the present invention.

In addition, cyclic olefin polymers manufactured by ring-opening polymerisation using a methathesis catalyst, such as molybdenum or tungsten, are included in polymers having olefinically unsaturated bonds.

In the hydrogenation reaction using the catalyst composition of the present invention, the olefinically unsaturated polymers may be hydrogenated in a condition where they are dissolved in a hydrocarbon solvent, or the olefinically unsaturated polymers maybe produced by polymerisation in a hydrocarbon solvent and may successively be hydrogenated.

Hydrocarbon solvents used in the hydrogenation reaction may be aliphatic hydrocarbons, e.g. pentane, hexane, heptane, octane, etc.; alicyclic hydrocarbons, e.g. cyclopentante, methyl cyclopentane, cyclohexane, or an aromatic solvent such as toluene. These hydrocarbon solvent may contain 20% by weight or a smaller amount of ethers such as diethyl ether, tetrahydrofuran, dibutyl ether, diethoxypropane, or dioxane.

There are no restrictions as to the concentration of polymers in carrying out the hydrogenation reaction of the present invention. Usually, however, the polymer concentration is in the range of from 1 to 30% by weight, and preferably in the range of from 3 to 20% by weight. The hydrogenation reaction is effected, after the addition of the hydrogenation catalyst composition under an inert gas atmosphere, e.g. in nitrogen or argon, or under a hydrogen atmosphere, by supplying hydrogen, with or without stirring while maintaining the temperature of the polymer solution at a specified temperature.

A temperature suitable for the hydrogenation reaction is in the range of from 0° C. to 150° C. A temperature lower than 0° C. is uneconomical, since at a temperature lower than 0° C. not only the catalyst activity is lowered, but also the rate of hydrogenation is retarded. If the temperature is higher than 150° C., on the other hand, not only the polymers tend to decompose or to gel, but also aromatic rings are hydrogenated at the same time, leading to a poor hydrogenation selectivity. A more preferred temperature is in the range of from 20° C. to 140° C., and most preferred in the range of from 50° C. to 130° C. In the hydrogenation reaction using the catalyst composition of the present invention, the reaction may be carried out at a comparatively higher temperature, resulting in a higher rate of reaction and a higher yield.

The hydrogenation reaction is carried out for a period of time in the range of from 1 minute to 5 hours. The larger the amount of the catalyst composition used and the higher the pressure, the reaction time may be shorter.

It will be appreciated that another aspect of the present invention is formed by the optionally substituted five membered heterocyclic titanium catalyst components (a) of formula I. These catalyst components (a) are novel compounds, which may be prepared by methods which are in principle known e.g. from F. Nieff, L. Richard and F. Mathey, Organometallics 1989 (8), 1473–1477, and F. Mathey, J. Organometal. Chem. 1990 (400) 149–164. More in particular the titanium compounds of formula I, wherein two optionally substituted phosphor or nitrogen containing five membered heterocyclics occur, are novel compounds.

The invention will now be illustrated by means of the following Examples which are included for illustrative purposes only and are in no way meant to limit the present invention.

EXAMPLES

Example 1

Preparation of hydrogen terminated poly(styrene)-poly (butadiene)-poly(styrene) block copolymer (SBS)

A 30 L batch of polystyrene-polybutadiene-polystyrene (SBS) block copolymer having an apparent molecular weight of 70,000 (as measured with gel chromatography (GPC) using polystyrene calibration standards) was prepared by sequential anionic polymerisation using secbutyl-ithium as the initiator in a stainless steel reactor. The polymerisation was conducted in cyclohexane, to which had been added 140 ppm of diethoxypropane at 18 wt % solids. The 1,2-content of the SBS polymer was 40%. At the end of the polymerisation reaction the reactor was sparged with hydrogen for 2 hrs to terminate the living SBS-Li polymer and produce SBS and LiH. The LiH content of the batch was determined to be 2.2 mmol/liter.

Example 2

Hydrogenation of SBS block copolymer with 2,5-diphenylphospholyl (cyclopentadienyl) titanium dichloride A stainless steel reactor was charged with 190 grams of SBS cement, prepared as in Example 1. The temperature of the reactor was fixed with 70° C. and the reactor was pressurised to 10 bar of hydrogen to saturate the cement. Meanwhile a suspension of 17 mg (40.5 mmol) of (2,5-diphenylphospholyl) (cyclopentadienyl) titaniumdichloride in 10 ml of cyclohexane was prepared. The catalyst suspension was added to the reactor and the hydrogen pressure was raised to 50 bar. The hydrogenation was allowed to run for 3 hours, during which period samples were drawn from the reactor and analysed by 1 H NMR to determine the conversion of the olefinic double bonds. Results are shown in Table 1.

Example 3

Hydrogenation of SBS block copolymer with (3,4-dimethyl phospholyl) (cyclopentadienyl) titanium dichloride Another hydrogenation run was performed in the same fashion as above, however, with the use of 12 mg (40.9 mmol) of (3,4-dimethylphospholyl) (cyclopentadienyl) titaniumdichloride. Results are shown in Table 1.

TABLE 1

| Run | 15 min conversion | 60 min conversion | 180 min conversion |
|---|---|---|---|
| Example 2 | 69 | 92 | 100 |
| Example 3 | 46 | 56 | 61 |

What is claimed is:

1. A catalyst composition suitable for hydrogenation of polymers containing ethylenical unsaturation which comprises at least:
   (a) a titanium compound of the formula

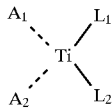

wherein $A_1$ represents an optionally substituted heterocyclic five membered ring comprising a phosphorous or nitrogen heteroatom, and $A_2$ has the same meaning as $A_1$ or alternatively represents an optionally substituted cyclopentadienyl group or indenyl group, and wherein $L_1$, and $L_2$ may be the same or different and each may be selected from hydrogen, halogen, lower alkyl, phenyl, aralkyl, having from 7 to 10 carbons, lower alkoxy group, phenyloxy, phenylalkoxy group having from 7 to 10 carbon atoms, carboxyl, carbonyl, a ~$CH_2P(Phenyl)_2$, —$CH_2$ Si(lower alkyl)$_3$ or ~$P(phenyl)_2$ group; and
   (b) an alkali metal hydride, added as such or prepared in situ in the polymer solution from the alkali metal terminated living polymer and/or from additionally added alkali metal alkyl.

2. The catalyst composition of claim 1 wherein the molar ratio of alkali metal: titanium is at least 2:1.

3. The catalyst composition of claim 1 wherein the alkali metal hydride is lithium hydride.

4. The catalyst composition of claim 3 wherein the molar ratio of lithium hydride to titanium is in the range of from 6 to 25.

5. The catalyst composition of claim 1 wherein ligands $L_1$ and $L_2$ in component (a) are selected from chlorine, bromine, carbonyl, methyl, ethyl, n-propyl, isopropyl, n-butyl, tert-butyl, sec-butyl, trimethylsilyloxy, benzyl, phenyl, hexyl, methoxy, ethoxy, n-propoxy, isopropoxy, butoxy, tert butoxy, sec butoxy, pentoxy, neopentoxy, phenoxy, phenylmethoxy, phenylethoxy or a $CH_2P(phenyl)_2$ group.

6. The catalyst composition of claim 5 wherein $L_1$ and $L_2$ are both chlorine, benzyl, phenyl, methoxy, ethoxy, isopropoxy, tert-butoxy, n-butoxy, phenoxy or a $CH_2P$ (phenyl)$_2$ group.

7. The catalyst composition of claim 6 wherein $L_1$ and $L_2$ are both chlorine.

8. The catalyst composition of claim 1 wherein component (a) is selected from (1-indenyl)(3,4-dimethylphospholyl) titanium dichloride, (1-indenyl) (3,4-dimethylphospholyl) titanium diphenoxide, (indenyl) (3,4-dimethylphos-pholyl), titanium dimethoxide, (cyclopentadienyl)(3,4-dimethylphospholyl) titanium dichoride (cyclopenta-dienyl)(2,5-diphenyl phospholyl) titanium dichloride, (cyclopentadienyl)(3,4-dimethylphospholyl) titanium dimethoxide, (cyclopentadienyl)(2,5-diphenyl-phospholyl)-titanium dimethoxide, (2-methylcyclopentadienyl) (3,4-dimethylphospholyl) titanium dichloride, (dimethoxycyclopentadienyl) (3,4-dimethylphospholyl) titanium dimethoxide, (3,4-dimethylcyclopentadienyl)(3,4-dimethylphospholyl) titanium dichloride, (1-methylindenyl) (3,4-dimethyl phospholyl) titanium dichloride, (5,6-dimethoxyindenyl) (3,4-dimethyl phospholyl)titanium dimethoxide, 1(methylindenyl)(3,4-dimethyl phospholyl) titanium dichloride, (5,6-dimethoxy-indenyl)(2,5-diphenyl phospholyl) titanium dimethoxide, (1methyl indenyl) (phospholyl) titanium dimethoxide, or (1-methyl indenyl) (phospholyl) titanium dichloride.

9. The catalyst composition of claim 1, which further comprises in addition to components (a) and (b) one or more promoters (c), selected from polar ketone compounds, hydroxy group containing ketone compounds, aldehyde compounds, ester compounds, lactone compounds, lactam compounds or epoxy compounds.

10. The catalyst composition of claim 9 wherein the one or more promoters are selected from ketone compounds, hydroxy group containing ketone compounds, aldehyde compounds, ester compounds or epoxy compounds.

11. The catalyst composition of claim 9 wherein the molar ratio of component (a) to component (c) is in the range of from 10 to 1/2.

12. The catalyst composition of claim 1 which further comprises, in addition to components (a) and (b), one or promoters (c), representing a reducing organic metal compound, selected from the group consisting of aluminium compounds, zinc compounds, and magnesium compounds.

13. The catalyst composition of claim 12 wherein the reducing organometal compound is selected from trimethyl aluminium, triethyl aluminium, tri-i-butyl aluminium, triphenyl aluminium, diethyl aluminium chloride, ethyl aluminium dichloride, methyl aluminium sesquichloride, ethyl aluminium sesquichloride, diethyl aluminium hydride, di-i-butyl aluminium hydride, tri(2-ethylhexyl) aluminium, aluminium tri-i-propoxide, aluminium tri-t-butoxide, diethyl aluminium ethoxide, diethyl zinc, bis(cyclopentadienyl) zinc, diphenyl zinc, dimethyl magnesium, diethyl magnesium, methyl magnesium bromide, methyl magnesium chloride, ethyl magnesium bromide, ethyl magnesium chloride, phenyl magnesium bromide, phenyl magnesium chloride, or t-butyl magnesium chloride.

14. The catalyst composition of claim 12 wherein the molar ratio of component (a) and (c) is in the range of from 1/1 to 1/18.

15. A process for the hydrogenation of polymers containing ethylenical unsaturation, comprising bringing a polymer solution in intensive contact with hydrogen in the presence of at least the catalyst composition according to any one of claims.

* * * * *